United States Patent
Johnson et al.

(10) Patent No.: US 7,551,058 B1
(45) Date of Patent: *Jun. 23, 2009

(54) SENSOR FOR MONITORING ENVIRONMENTAL PARAMETERS IN CONCRETE

(75) Inventors: Eric Arthur Johnson, Greene, NY (US); Joseph Duane Kulesza, Binghamton, NY (US)

(73) Assignee: Advanced Design Consulting USA, Inc., Lansing, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/732,717

(22) Filed: Dec. 10, 2003

(51) Int. Cl.
*H04Q 5/22* (2006.01)
(52) U.S. Cl. .................. 340/10.41; 340/665; 709/213
(58) Field of Classification Search .............. 340/10.41, 340/665, 686, 572.1, 572.5, 666; 709/213; 324/664, 634
See application file for complete search history.

(56) References Cited

U.S. PATENT DOCUMENTS

| | | | |
|---|---|---|---|
| 4,703,253 A | 10/1987 | Strommen | |
| 5,563,341 A | 10/1996 | Fenner et al. | |
| 5,627,749 A | 5/1997 | Waterman et al. | |
| 6,393,921 B1 | 5/2002 | Grimes et al. | |
| 6,397,661 B1 | 6/2002 | Grimes et al. | |
| 6,617,963 B1 * | 9/2003 | Watters et al. | 340/10.41 |
| 6,639,402 B2 | 10/2003 | Grimes et al. | |
| 6,690,182 B2 * | 2/2004 | Kelly et al. | 324/700 |
| 6,720,866 B1 * | 4/2004 | Sorrells et al. | 340/10.4 |
| 7,038,470 B1 * | 5/2006 | Johnson | 324/664 |
| 2004/0113790 A1 * | 6/2004 | Hamel et al. | 340/572.1 |
| 2005/0033819 A1 * | 2/2005 | Gambino et al. | 709/213 |

OTHER PUBLICATIONS

Al-Qadi, I.L. et al. (1997) Design and Evaluation of a Coaxial Transmission Line Fixture to Characterize Portland Cement Concrete. Construction and Building Materials 11(3):163-173.
Bariain, C. et al. (2000) Optical Fiber Humidy Sensor Based on a Tapered Fiber Coated With Agarose Gel. Sensors and Actuators B 69: 127-131.
Budtova, T. et al. (2001) Hydrogel Suspensions as an Electro-Rheological Fluid. Polymer 42: 4853-4858.

(Continued)

*Primary Examiner*—Timothy Edwards, Jr.
(74) *Attorney, Agent, or Firm*—Leo B. Kriksunov; Anne M. Schneiderman

(57) ABSTRACT

The invention provides a sensor for monitoring an environmental parameter in concrete comprising an enclosure for embedding in concrete; a detecting means connected to the enclosure for detecting at least one environmental parameter in concrete, the detecting means comprising at least one capacitive element for measuring capacitive change; an active material connected to the enclosure, the active material being liable to respond to the environmental parameter and the active material being operably connected to the capacitive element; a RFID chip mounted within the enclosure, the RFID chip being operably connected to the detecting means; and an antenna operably connected to the RFID chip, the antenna being operably connected to the detecting means, and the antenna being part of an L-R-C circuit whose resonance frequency shifts within an assigned frequency band. The invention also provides a MEMS-based capacitor that responds to an environmental parameter in concrete.

20 Claims, 8 Drawing Sheets

OTHER PUBLICATIONS

Dec, A. et al. (1998) Micromachined Electro-Mechanically Tunable Capacitors and Their APplications to RF IC's. IEEE Transaction on Microwave Theory and Techniques 46 (12): 2587-2596.

Fenner, R.L. et al. (1997) HMX2000—A Shear/Stress MEMS Hygrometer. Detroit (Michigan) Sensors Expo '97: 13 pp.

Fenner, R.L. et al. (2000) MEMS Humidity Sensor: Report On Test and Appication. May 2000 Sensors Expo (Anaheim, California): 4pp.

Fernanades, R. et al. (2003) Electrochemically Induced Deposition of a Polysaccharide Hydrogel onto a Patterned Surface. Langmuir 19: 4058-4062.

Gupta, B.D. et al. (2001) A Novel Probe for a Fiber Optic Humidity Sensor. Sensors and Actuators B 80: 132-135.

International Road Dynamics Inc., Saskatoon, Saskatchewan, Canada (2002) Concrete Maturity Monitor: Wireless Technology In the Palm of Your Hand. Jun. 2002 (Rev A): 2 pp.

Johnson, B. et al. (2004) Experimental Techniques for Mechanical Characterization of Hydrogels at the Microscale. Experimental Mechanics 44(1): 1-8.

Johnson, B. et al. (2002) Mechanical Properties of a pH Sensitive Hydrogel. Society for Experimental Mechanics, 2002 SEM Annual Conference Proceedings, Milwaukee, WI: 4 pp.

Kharaz, A. et al. (1995) A Distributed Optical-Fibre Sensing System for Multi-Point Humidity Measurement. Sensors and Actuators A 46-47: 491-493.

Khijwania, S.K. et al. (1998) Fiber Optic Evanescent Field Absorption Sensor with High Sensitivity and Linear Dynamic Range. Optics Communications 152: 259-262.

Kim, S.J. et al. (2003) Electrical/pH Sensitive Swelling Behavior of Polyelectrolyte Hydrogels Prepared with Hyaluronic Acid-Poly (vinyl alcohol) Interpenetrating Polymer Networks. Reactive and Functional Polymers 55: 291-298.

Krantz, D. et al. (1999) Project Update: Applied Research on Remotely-Queried Embedded Microsensors. SPIE Proceedings 3573: 157-164 (Smart Structures and Materials 1999: Smart Electronics and MEMS, Paper No. 3672-14).

Livingston, R.A. (1999) FHWA Fiber-Optics Research Program: Critical Knowledge for Infrastructure Improvement. Public Roads (Federal Highway Administration) 63(1) (Jul./Aug. 1999): 10 pp.

Microchip Technology Inc., Mountain View, California (2002) MCRF355/360: 13.56 MHz Passive RFID Device with Anti-Collision Feature. Publication DS21287F: 1-8.

Microchip Technology Inc., Mountain View, California (1997) Sensor Interface : Transponder. Publication DS40160A/3_001: 3-3 to 3-4.

Millard, S.G. et al. (2001) Coaxial Transmission Lines: Development of Test Procedures for Concrete. Journal of Materials in Civil Engineering May/Jun. 2001: 202-208.

Ong, K.G. et al. (2001) Design and Application of a Wireless, Passive, Resonant-Circuit Environmental Monitoring Sensor. Sensors and Actuators A 93: 33-43.

Ong, K.G. et al. (2002) A Wireless, Passive Carbon Nanotube-Based Gas Sensor, IEEE Sensors Journal 2(2): 82-88.

Strain Monitor Systems, Inc., San Diego, California (2000) SMG032: Dual-Peak Output Structural Health Sensors (Nov. 2000): 1p.

Varadan, V.K. et al. (2000) Design and Development of a Smart Wireless System for Passive Temperature Sensors. Smart Mater. Struct. 9: 379-388.

* cited by examiner $$\Phi = \frac{A \cdot \mu_0 I_R r_R^2}{2(r_R^2 + x^2)^{3/2}}$$

$$\Phi = \frac{\pi \cdot \mu_0 \mu_R \cdot I_R N_R d^2}{4 \cdot l}$$

FIG. 3

SENSOR FOR MONITORING ENVIRONMENTAL PARAMETERS IN CONCRETE

CROSS-REFERENCE TO RELATED APPLICATIONS

Not applicable

STATEMENT REGARDING FEDERALLY SPONSORED RESEARCH OR DEVELOPMENT

Not applicable

REFERENCE TO APPENDIX

Not applicable

1. TECHNICAL FIELD

The present invention relates to sensors for monitoring concrete condition. The invention also relates to sensors that measure environmental parameters in concrete such as moisture content, temperature, pH and concentrations of ions such as chloride, sodium or potassium.

2. BACKGROUND OF THE INVENTION

With infrastructure costs escalating, it is becoming essential to monitor and/or evaluate the health of concrete structures so that timely maintenance can maximize their useful lives. The initial strength and the service life of concrete used in an infrastructure, e.g., a roadway or a bridge, is significantly affected by its moisture content from the time that it is placed onwards. Moisture and temperature are the primary drivers for the hydration of Portland cement, and are essential factors in the most prevalent deteriorative processes, such as damage due to freezing and thawing, alkali-aggregate reaction, sulfate attack or delayed Ettringite formation.

One of the most devastating, yet most common, forms of concrete degradation is corrosion of embedded reinforcing steel, which is driven by moisture and temperature as the pH is lowered. Swelling of alkali-silicate gels, driven by sodium and potassium, is an additional failure mechanism in concrete.

In normal concrete that has not been contaminated by deicing salts or sea salt, steel (iron) is protected against corrosion by the passive nature of the high pH environment characteristic of Portland cement concrete. (Porewater in hardened concrete is often modeled as a saturated calcium hydroxide solution with a pH of 13+.) This natural passivity is the reason that steel-reinforced concrete is a chemically stable combination of materials. This balance is upset, however, when contaminants such as deicing salts penetrate the concrete or when concrete carbonates, formed by the conversion of calcium hydroxide to calcium carbonate, as $CO_2$ permeates the capillary pores. Many different tests, summarized in Table 1, are currently required to provide complete data throughout the life of concrete.

TABLE 1

Tests of Concrete Condition

| Stage in concrete production, construction, and service life | Temperature | Moisture Content | pH | Chloride concentration |
|---|---|---|---|---|
| Stockpiles of raw materials | Compute requirements for heated or chilled water based on required concrete delivery temperature and stockpiled materials temp. Check against common problem of hot cement due to insufficient cooling in the mfg. Process. Identify cement composition by adiabatic temperature-time ("Heat Signature" of cementitious paste). | Measure aggregate moisture content for water adjustment in batching process. | Evaluate cement type by pH-time record, based on differing rates of $Ca(OH)_2$ release by $C_2S$ and $C_3S$. Measure pH of mix water: affects cement hydration and admixture behavior. | Determine chloride concentration of aggregates, mix water, and admixtures for compliance with building code maximum values (ACI 318, ACI 222). Check for aggregates that are contaminated with salt from marine deposits. Check that such aggregates have been washed as required. |
| Mixing, transport, and placing concrete | Check for compliance with minimum and maximum temperature specification requirements (ACI 301, 305, 306) Check that the mixture composition is as specified by field calorimetry ("heat signature of concrete"). | Estimate water content of fresh concrete, currently by AASHTO microwave oven test, AC Impedance, or nuclear methods. | Document high pH of fresh concrete for demonstrating safety hazard and need for protection | Determine chloride concentration in fresh concrete (regardless of $Cl^-$ source) for compliance with building code maximum values (ACI 318, ACI 222). Quality control (Q/C) check to make sure that non-chloride admixtures have been used when required. Q/C check to make sure seawater not used when prohibited. |
| Recently cast concrete. (1-4 hours) | Predict setting time from concrete temperature via maturity principle. Check for compliance | Monitor rate of surface drying to prevent or minimize plastic shrinkage cracking Monitor effectiveness of | Monitor rate of carbonation ($CO_2$) diffusion into surface of concrete that can result in dusting and | |

TABLE 1-continued

Tests of Concrete Condition

| Stage in concrete production, construction, and service life | Temperature | Moisture Content | pH | Chloride concentration |
|---|---|---|---|---|
| | with maximum or minimum in-place concrete temp. specifications (ACI 305, 306) Estimate rate of evaporation via evaporative cooling in arid environments. Estimate rate of early-age strength gain via maturity method. | actions taken to prevent moisture loss. (See ACI 308 Guide to Curing Concrete, Ch. 4) | make concrete surfaces unpaintable. (Common problem when temporary heaters are not externally vented, ACI 306) | |
| Recently hardened concrete. (12 hours to 7 days) | Temperature-time record used to predict strength via maturity. Check for compliance with maximum or minimum in-place concrete temperature specs (ACI 305, 306). Check for compliance with maximum temperature difference requirements, within or between adjacent members. (ACI 207). | Continue to monitor effectiveness of actions take to prevent moisture loss. (See ACI 308 Guide to Curing Concrete, Ch. 4) | Continued monitoring of carbonation. Observe effectiveness of fly ash, ground blast-furnace slag, silica fume and other pozzolans in reacting with and neutralizing $CA(OH)_2$ | |
| Over useful service life of concrete. | Temperature used to infer rate of deteriorative processes: alkali-aggregate reaction, sulfate attack, delayed Ettringite formation, (Arrhenius-type exponential temperature influence). Monitor internal temperature to estimate onset of freezing or to determine freezing point. Infer presence of freezable water from internal temperature. | Evaluate water vapor transmission and suitable for application of flooring materials. Evaluate effectiveness of external or internal water-proofing measures. Evaluate effectiveness of traffic-bearing membranes and sealers, vapor barriers. Evaluate moisture effects on alkali-aggregate reaction, sulfate attack and delayed Ettringite formation, freezable water for frost damage. | Evaluate effect of pH on steel passivity. Measure depth of carbonation (now done with phenolphthalein indicator). | Compare to chloride ion concentration threshold values for initiation of corrosion. Evaluate effectiveness of electrochemical chloride removal. |

Hardened concrete has long been evaluated by laboratory wet analysis of extracted samples. While these techniques have been widely accepted, they are time-consuming and expensive. Electronic moisture sensors have been available for a considerable time, but have inherent limitations when embedded within concrete. The highly alkali environment can damage their electronics, and they are sensitive to electromagnetic noise. A further drawback of this approach is that power must be provided from an external source, requiring cables and connectors (e.g., Structural Health Sensor, Strain Monitor Systems, Inc., San Diego, Calif. 92101), or from an internal battery (e.g., Wireless Concrete Maturity Monitor, International Road Dynamic, Inc. Saskatoon, Saskatchewan, Canada). This necessarily increases the sensor's size and decreases the sensor's useful life.

Fiber-optic techniques have been proposed as an alternative means of evaluating concrete degradation. Several different techniques using optical fibers have been demonstrated for measuring moisture content. These techniques fall into two broad categories: (i) intensity measurements that take advantage of changes in light absorption as a function of moisture content, and (ii) measurements that rely on a change in the index of refraction. Within these categories, both single-mode and multi-mode fibers have been used, and various means to separate temperature and humidity effects have been employed. By using Time Domain Reflectography (TDR), multiple sensors have been monitored on a single fiber. The drawback of this approach is that only up to six sensors have been used. This somewhat decreases the cost of this type of sensor, but this is offset by the sophistication and cost of the equipment required for analysis.

Furthermore, these optical systems all have the drawbacks that they require laser sources and optical power meters for measurements, as well as sophisticated analysis, if multiple sensors are to be interrogated using TDR. If left in place, the equipment represents a considerable expense and can be vulnerable to environmental damage. If equipment must be carried to a site and connected to the fiber optic sensors, then set-up and analysis time can be lengthy, again adding to the expense.

Low-powered (e.g., nano-watt) electronic devices offer a possible solution, but in their current state of development, also have drawbacks. Even though they are low-powered, they have a limited life, particularly when they are powered by batteries.

2.1 Evaluation of Environmental Parameters in Concrete

Currently, concrete integrity or condition is evaluated primarily by extracting samples for wet chemical analysis in the laboratory where environmental parameters in the concrete, e.g., its moisture content, pH and ionic concentrations (e.g., concentrations of chloride, sodium or potassium ions) can be measured. Concrete samples are typically obtained by time-consuming and expensive methods, e.g., either pulverizing pieces cut form the hardened concrete, or by collected the dust from drilling holes in the concrete to prescribed depths.

Another environmental parameter, temperature, is evaluated in fresh concrete by ASTM C1064 (Standard Test Method for Temperature of Freshly Mixed Portland Cement Concrete). Evaluating the temperature of hardened concrete, such as recording the temperature-time history to estimate concrete properties as a function of the maturity, is most conveniently done by embedded thermocouples connected to data loggers. Pre-programmed data loggers known as "maturity meters," are often used.

The maturity method estimates the degree to which the Portland cement has been hydrated, by recognizing a simple linear relationship between concrete temperature and the rate of cement hydration (known as the Nurse-Saul approach), or the more accurate non-linear Arrhenius reaction rate model proposed by Freiesleben-Hansen and Pederson. In either case, the normal assumption is that sufficient water is available to hydrate the cement, and moisture content data are not normally collected, nor are maturity estimates corrected when there is a lack of available water.

The drawback of the maturity method is that thermocouples are subject to corrosion and require instrumentation that is expensive and sensitive to the environment (and that therefore should not remain on-site). The maturity method is also an empirical model with considerable uncertainty, i.e., it gives only information on the state of hydration.

Moisture content of aggregates is currently determined by oven-drying techniques (conventional, microwave, or convection oven). Alternatively, electrical conductivity-based moisture meters may be permanently mounted in concrete batching plants. Another technique employs a "Speedy Moisture Meter," which combines a wet or damp sand with a fixed amount of calcium carbide powder in a reaction chamber. A pressure gauge indicates the amount of acetylene gas generated, and thus infers the initial available moisture. The drawback of techniques that use oven-drying or moisture meters is that core samples must be taken from the concrete, which is time-consuming, expensive, requires skilled laboratory technicians, leaves openings that may not have been sealed, and which can allow water and salts ingress into the concrete.

Moisture content in hardened concrete can be estimated by removing samples of concrete and oven-drying them. Water-vapor transmission is estimated by collecting water on one face of the concrete (often with a desiccant such as calcium chloride.) Embeddable moisture gauges, also known as "internal humidity meters" have been built and used by several researchers, but are not routinely used (See ACI 308 Guide to Curing Concrete, Chapter 4, "Monitoring Curing Effectiveness.")

pH measurements in fresh concrete were conducted by Thomas and Hover at Cornell in 1988 to evaluate the rate of $Ca(OH)_2$ production due to cement hydration, using a conventional electronic pH meter. The drawback of this approach is that the viscous cement paste tended to clog the tip of the pH probe, making it difficult to record the continuously changing pH.

In hardened concrete, the most common pH evaluation technique is to spray phenolphthalein indicator on a concrete surface that has been freshly exposed by drilling, cutting, or cracking. Concrete that does not produce the characteristic pink/purple color is considered to have become acidified (most typically by ingress of $CO_2$). The drawback of this approach is that it requires core samples be taken from the concrete. Also, this technique is qualitative rather than quantitative, in that it merely indicates whether pH is basic or acidic.

Chloride is extracted from concrete for analysis by either distilled water or acid to obtain the water-soluble or acid-soluble chloride concentration. The solution is then analyzed by any of a number of wet-chemistry lab methods (See ASTM C1152/C114.) Again, the drawback of this approach is that it requires extraction of chloride from the concrete, which is time-consuming, expensive and involves complex wet-chemistry diagnostic tests.

Assessment of the corrosion of steel reinforcing bars in concrete is commonly carried out by Linear Polarization Resistance (LPR), half cell potential, macrocell current measurements, or resistivity tests.

2.2 Embeddable Concrete Sensors

Although the above-described techniques are in wide use, they are necessarily time-consuming and expensive. The obvious advantages of in-situ testing have led to the development of embeddable sensors.

One type of embeddable sensor currently available is a half cell. A half cell potential survey can be conducted of reinforced concrete structures known, or believed to be, suffering from corrosion, particularly due to chloride contamination. Half cells are also embedded in concrete to monitor the performance of cathodic protection systems for atmospherically exposed steel in concrete, although the size of existing devices can make this difficult. The drawbacks of this approach (which is generally used only in buildings) are size, complexity and cost of these devices, plus external power requirements and need for read-out.

Another type of embeddable sensor currently available is a fiber-based moisture sensor. Fiber-based moisture sensors have recently been developed based on the technology for monitoring strain in bridges using optical fibers with Bragg diffraction. Jones and Kharaz used a multi-mode fiber with evanescent absorption in a gelatinous cladding layer to detect changes in moisture content (Jones and Kharaz, "A distributed optical-fibre sensing system for multi-point humidity measurement," Sensors and Actuators A 46-47 (1995) 491-493). They report that the reversible hydration of cobalt chloride within the gelatin significantly changed the absorption of light at a wavelength of 670 nm while absorption at 850 nm was nearly unchanged. By using these two wavelengths, the effects of temperature were removed from the measurement of moisture content and a resolution of <2% was achieved. Although the authors claimed a useful range of humidity from 20 to 80%, the results showed that the range can be increased to 100% albeit with a reduction in the resolution. The drawback of this technique, however, is that the fibers remain embedded but read-out requires a laser source, a detector, and electronics that are expensive and sensitive to the environment (and that therefore should not remain on-site). Connecting to optical fibers is difficult, owing to the precise alignment that is required. All of the fiber-optic techniques share these drawbacks.

Bariáin et al. measured moisture content using a refractometer comprising a single-mode fiber with a double tapered section that was coated with agarose gel (Bariáin, Matáas, Arregui and López-Amo, "Optical fiber humidity sensor based on a tapered fiber coated with agarose gel," Sensors and Actuators B 69 (2000) 127-131). As the refractive index changed with increasing moisture, attenuation across the tapered section was reduced. Results were presented for a range of 30% to 80% relative humidity (RH) but the range may be extended with some loss of sensitivity. The RH of concrete, however, can approach 100% at times, which limits the usefulness of such a refractometer. Furthermore, sensitivity to temperature was not measured.

Jindal et al. used a moisture-sensitive core within a section of single-mode fiber to increase the evanescent absorption as the sensor is traversed by light (Jindal, Tao, Singh and Gaikwad, "A Long Range, Fast-responsive Fiber Optic Relative Humidity Sensor," Optical Engineering 41, 5 (2002) 1093-1096).

An embeddable electronic device from Virginia Technologies, Inc. (Charlottesville, Va.) can measure LPR, open circuit potential (OCP), resistivity, chloride ion concentration [Cl—] and temperature. Its drawback, however is that it must be connected to a data logger that also provides the unit with power.

An embeddable sensor to measure resistivity within concrete is also available (The Applied Physics Lab, The Johns Hopkins University). The device is wireless and powered by an RF source that also stores data for subsequent processing and analysis. Its primary drawback, however, is that it is unable to measure other parameters of interest. It also has the drawbacks of large antenna size and requirements for a particular orientation.

2.3 Passive Sensors

The sensors described in Section 2.2 may all be described as active, requiring continuous power from a battery or an external source in order to function. Passive sensors that operate by changes in the capacitive or inductive elements have also been proposed. Ong and his colleagues have developed passive sensors to evaluate temperature, humidity and pressure, the complex permittivity of the surrounding medium and the concentration of $CO_2$, $NH_3$ and $O_2$ (Ong, Zeng and Grimes, "A Wireless, Passive Carbon Nanotube-based Gas Sensor," IEEE Sensors Journal, 2, 2, (2002) 882-88; Ong, Grimes, Robbins and Singh, "Design and application of a wireless, passive, resonant-circuit environmental monitoring sensor," Sensors and Actuators A, 93 (2001) 33-430). These devices operate in the range of 5 to 25 MHz and rely on changes in impedance. The operating distance was typically limited to under 10 cm.

Varadan et al. used a Surface Acoustic Wave (SAW) device operating at 915 MHz to measure temperature (Varadan, Teo, Jose and Varadan, "Design and development of a smart wireless system for passive temperature sensors," Smart Mater. Struct. 9 (2000) 379-388). This device does not rely on measuring the impedance at the RF transmitter but rather uses the delay time between the emitted and returned signals. A frequency modulated RF wave is transmitted to the sensor and the induced current is converted to an acoustic wave that traverses the surface of a lithium niobate wafer, is converted back into an electrical signal and re-radiated by the antenna. The delay time is a function of the temperature of the wafer and the system resolution is 0.33° C. Measurements can be made over a range of one to two meters.

Butler et al. used a change in the inductance of the sensor's antenna rather than a change in capacitance to measure strain (Butler, Vigliotti, Verdi and Walsh, "Wireless, passive, resonant-circuit, inductively coupled, inductive strain sensor," Sensors and Actuators A, 102 (2002) 61-66). A coil antenna was deformed in-plane to change its inductance and shift the resonance frequency. In other respects it operates similarly to the devices previously described.

Milos et al. (Milos et al., "Wireless Subsurface Microsensors for Health Monitoring of Thermal Protection Systems on Hypersonic Vehicles", in Advanced Nondestructive Evaluation for Structural and Biological Health Monitoring, Ed. T. Kundu, Proceedings of SPIE 4335 (2001) 74-82) successfully combined a passive sensor with an RFID chip to produce a device that signals when a certain temperature has been exceeded. Two capacitors were attached in parallel with the antenna with one of the capacitors connected by a fusible link designed to melt at 292° C. The shift in resonance frequency was used to read the device while its location was determined from its identification number. In another version, the fusible link causes the transponder bit-stream to be inverted when it is broken. A device using this second version has been commercialized by SRI International and used to identify heat-shield tiles on the space shuttle whose adhesive may have been damaged during re-entry.

Those devices that measure the change in resonance frequency offer good sensitivity to a wide range of important phenomena and can potentially be used as concrete sensors. It is unfortunate but inevitable that their operating range is short, however, owing to the rapid reduction in mutual inductance with separation.

2.4 RFID Systems

As discussed above, low-powered electronic devices for monitoring concrete have a limited life, particularly when they are powered by batteries. By contrast, so-called Radio Frequency Identification (RFID) devices combine a microchip with an antenna (the RFID chip and the antenna are collectively referred to as the "transponder" or the "tag"). The antenna provides the RFID chip with power when exposed to a narrow band, high-frequency electromagnetic field. Such a device can return a unique identification ("ID") number by modulating and re-radiating the radio frequency (RF) wave. The basic design of an RFID chip is extremely simple, containing only basic modulation circuitry, a rectification bridge and non-volatile memory.

RFID systems are gaining wide use due to their low cost, indefinite life and the ability to identify parts at a distance without contact. RFID systems are in widespread use for asset management, inventory, pallet tracking, electronic tolls, livestock tracking, building access and automobile security. They first appeared in tracking and access applications during the 1980s. Since these are wireless systems that allow non-contact reading, they may be used in manufacturing and other hostile environments where barcode labels could not survive.

The simplest RFID system provides one-way communication between an RFID transponder (i.e., an RFID chip and antenna) and a transceiver. A dipole antenna or a coil, depending on the operating frequency, is connected to the RFID chip and powers it when current is induced in the antenna by an RF signal from the transceiver's antenna.

Within the United States, commonly used operating bands for RFID systems center on one of three government-assigned frequencies: 125 KHz, 13.56 MHz or 2.45 GHz. A fourth frequency, 27.125 MHz, has also been assigned. Of these frequencies, only the GHz range provides a true RF link, while the others operate as electromagnetic transformers.

When the 2.45 GHz carrier frequency is used, the range of an RFID chip can be many meters. While this is useful for remote sensing, there may be multiple transponders within the RF field. In order to prevent these devices from interacting and garbling the data, however, anti-collision schemes must be used.

Since an infrastructure may remain in place, or have a useable lifetime of a hundred years or more, there is a need in the art for an embeddable sensor for monitoring concrete condition that can survive for the lifetime of the concrete. Furthermore, there is a need in the art to provide embeddable concrete sensors that can be used to detect changes in environmental parameters in concrete such as moisture content, temperature, pH, and the concentration of ions (e.g., chloride, sodium and potassium ions). Such sensors could provide critical data for monitoring the condition of concrete, starting with the initial quality control period of freshly mixed or freshly cast concrete, through the concrete's useful service life, and through its period of deterioration and/or repair.

Citation or identification of any reference in Section 2, or in any other section of this application, shall not be considered an admission that such reference is available as prior art to the present invention.

3. SUMMARY OF THE INVENTION

The present invention provides an embeddable sensor for monitoring concrete condition that can survive for the lifetime of the concrete. The invention is based on the surprising discovery, on the part of the inventors, that a low-cost, efficient, long-lived sensor for monitoring concrete may be constructed that is powered and interrogated using radio frequency (RF) energy from a distance (e.g., a distance of over one meter), and that returns a unique identification signal (e.g., a number) so that data can be correlated with sensor location. According to the invention, operation of the sensor is based on capacitive changes in a MEMS semi-conductor device (e.g., a silicon semi-conductor device) by a change in (e.g., swelling of or change in permittivity of) a material deposited on or in the semi-conductor device. Data obtained from the sensor of the invention is used to prolong the service life of concrete, lower infrastructure costs and promote development of more effective plans for remediation.

The invention provides a sensor for monitoring an environmental parameter in concrete comprising an enclosure for embedding in concrete; a detecting means connected to (e.g., mounted within or mounted on the surface of) the enclosure for detecting at least one environmental parameter in concrete, the detecting means comprising at least one capacitive element for measuring capacitive change; an active material connected to (e.g., mounted within or mounted on the surface of) the enclosure, the active material being liable to respond to the environmental parameter and the active material being operably connected to the capacitive element; a RFID chip mounted within the enclosure, the RFID chip being operably connected to the detecting means; and an antenna operably connected to the RFID chip, the antenna being operably connected to the detecting means and being part of an L-R-C circuit whose resonance frequency shifts within the assigned frequency band.

In one embodiment, the sensor further comprises a transceiver electromagnetically coupled with the antenna. In another embodiment, the sensor further comprises an information processor in communication with the transceiver. In one aspect of this embodiment, the information processor is adapted to identify the environmental parameter from data generated by the transceiver. In another embodiment, the environmental parameter is identified by measuring a shift in frequency of complex impedance (Z) within the assigned frequency band.

In another embodiment, the transceiver is operably connected (e.g., by a wired or wireless connection) to a means for measuring the change in resonance frequency (i.e., frequency shift) of the sensor's L-R-C circuit (where L is the antenna's inductance, R is resistance and C is capacitance).

In another embodiment, the change in resonance frequency is a shift in frequency of a re-radiated signal.

In another embodiment, the shift in frequency is caused by a change in capacitance.

In another embodiment, the capacitive change is effected by movement of the capacitive element.

In another embodiment, the capacitive change is effected by change in permittivity of the active material.

In another embodiment, the capacitive element comprises a parallel plate capacitor.

In another embodiment, the parallel plate capacitor is a perforated parallel plate capacitor.

In another embodiment, the capacitive element comprises an interdigitated capacitor.

In another embodiment, at least a portion of the enclosure is permeable.

In another embodiment, the environmental parameter is moisture content. In another embodiment, the environmental parameter is temperature. In another embodiment, the environmental parameter is pH. In another embodiment, the environmental parameter is ion concentration. In specific embodiments, the ion is chloride, sodium or potassium ion.

In another embodiment, the assigned frequency band is 13.56 MHz and the re-radiated signal is within a frequency band 27.125 MHz.

In another embodiment, the active material is a dielectric material.

In another embodiment, the active material is a hydrogel.
In another embodiment, the antenna is a coil antenna.
In another embodiment, the antenna is a loop antenna.
In another embodiment, the antenna is a dipole antenna.
In another embodiment, the antenna is connected to (e.g., mounted within or mounted on the surface of) the enclosure.
In another embodiment, the antenna is wrapped around the enclosure.

The invention also provides a MEMS-based capacitor that responds to an environmental parameter in concrete.

The invention also provides a method for applying an active material within a MEMS device comprising pouring at least one precursor material of the active material into an opening of the MEMS device.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1 shows a schematic diagram of an embodiment of the sensor of the invention. In this embodiment, the sensor comprises a RFID chip, a ferrite core antenna, a capacitive element and a diode. The diode produces harmonics of the excitation frequency. See Section 5.5 for details.

FIG. 2. RFID antenna-capacitor circuit. L1 is the sensor antenna coil, C1 is a fixed capacitor, C2 is the variable capacitance formed by the sensor, which is the variable capacitor sensitive to the environment. C2 is switched out of the resonant circuit by the RFID chip using the internal transistor as it transmits its data. This action causes the resonance of the LC circuit formed by the antenna and capacitors to change, the change from resonance to non-resonance is detected at the reader as a voltage drop in the source antenna. However, it is the shift of the primary resonant frequency that allows the measurement a change in capacitance at C2. That is, the difference between the theoretical center frequency with C2 at some nominal value and the frequency at which the actual resonant frequency is found. This difference is used to infer a difference in capacitance at C2 and therefore a proportional difference in the environment. See Section 5.4.1 for details.

FIG. 3 is a diagram showing magnetic flux Φ for a single-loop antenna (top half of diagram) and a ferrite-core antenna (bottom half of diagram). See Section 5.5 for details.

Figure 5:
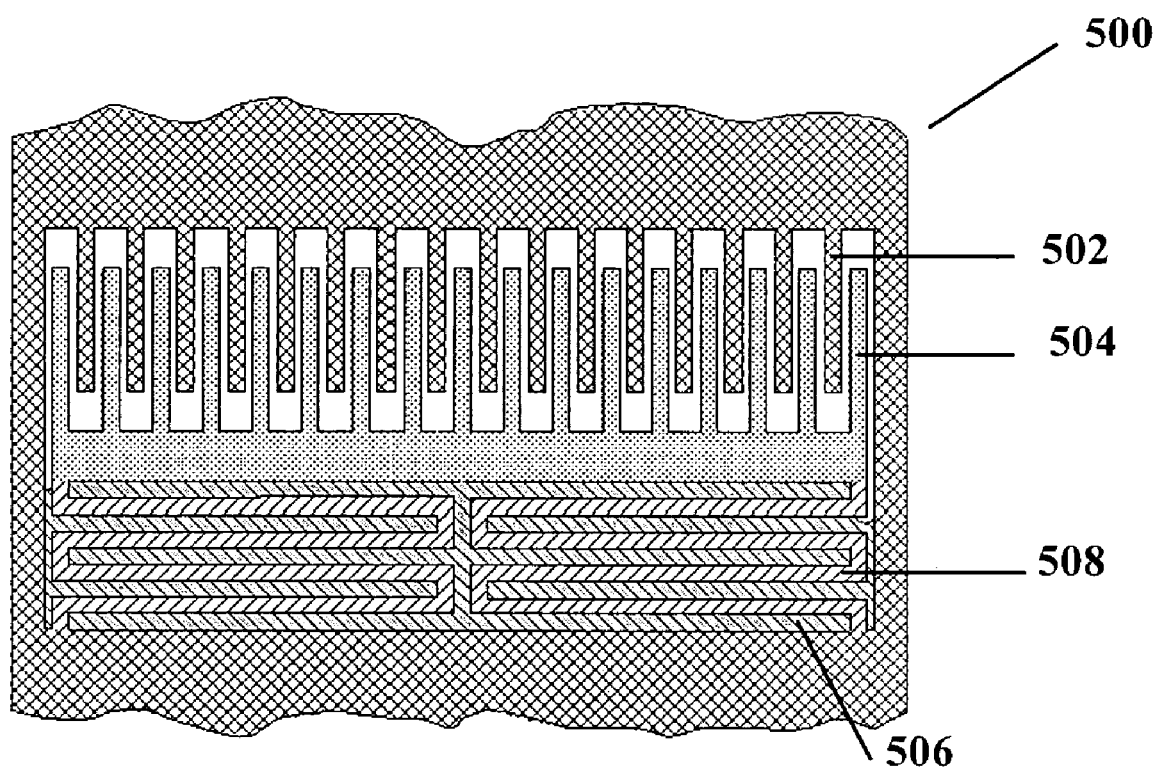

FIG. 5 is a schematic diagram of the top view of an embodiment of a sensor of the invention comprising a MEMS device 500. The MEMS device forms the capacitive element of an L-R-C network (not shown). Two sets of interdigitated capacitive elements, 502 and 504, are formed within the MEMS device 500 with the first of these, 502, fixed within the device and the second, 504, movably mounted on spring elements 508. The active material 506 (e.g., hydrogel) is disposed within and between the spring elements 508. This active material is chosen so that it responds to a measurand by swelling. As swelling occurs, capacitive element 504 moves relative to the fixed capacitive element 502, thereby changing the capacitance of the device. An important feature of this embodiment is the degree to which the active material 506 is constrained. The ratio of the surface bounded by the body of the MEMS device 500, the spring elements 508 and the movable capacitive element 504 to the free surface above and below the active material 506 is extremely high. As a consequence, the force that can be exerted by the active material is extremely high.

Figure 6:
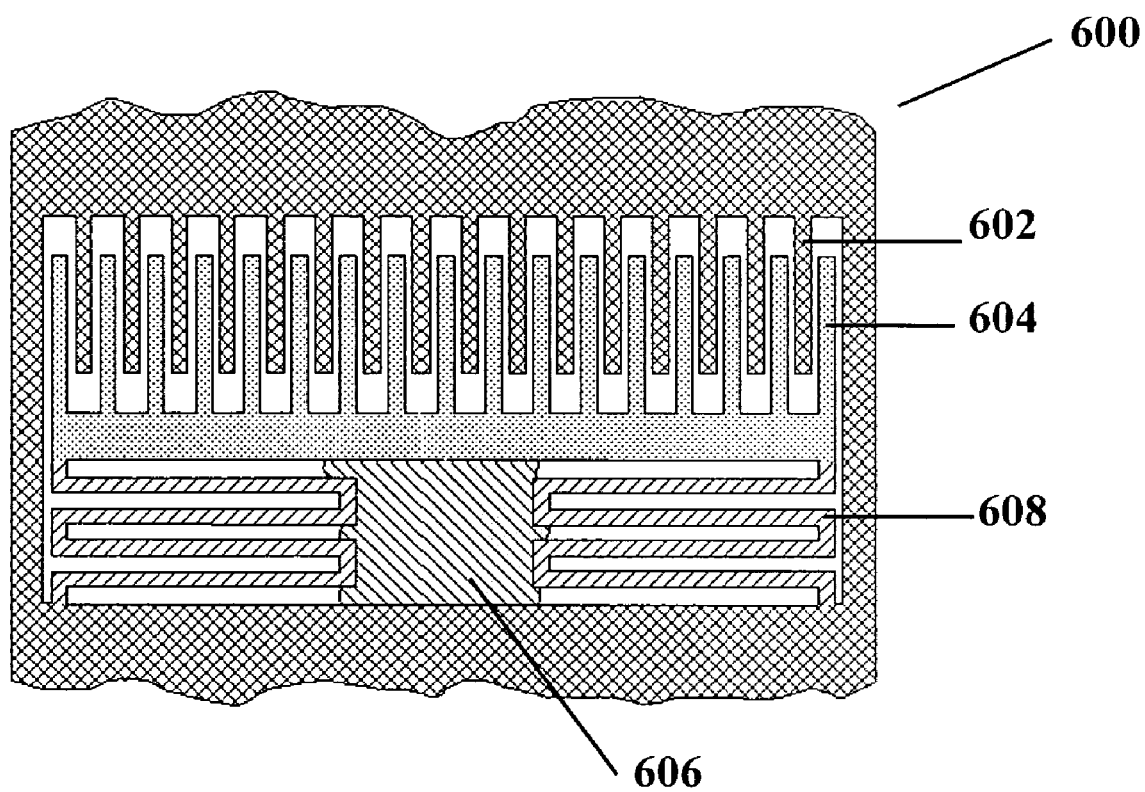

FIG. 6 shows a schematic diagram of the top view of another embodiment of a sensor of the invention comprising a MEMS device 600. The MEMS device forms the capacitive element of an L-R-C network (not shown). Two sets of interdigitated capacitive elements, 602 and 604, are formed within the MEMS device 600 with the first of these, 602, fixed within the device and the second, 604, movably mounted on spring elements 608. The active material 606 (e.g., hydrogel) is disposed between the main body of the MEMS device 600 and the movable capacitive element 604. This active material is chosen so that it responds to a measurand by swelling. As swelling occurs, capacitive element 604 moves relative to the fixed capacitive element 602, thereby changing the capacitance of the device. An advantage of this embodiment is the ease with which the active material 606 can be deposited. There is, however, a reduction in the amount of force that can be applied to movable capacitive element 604, due to the reduction in the degree of constraint in material 606.

Figure 7:
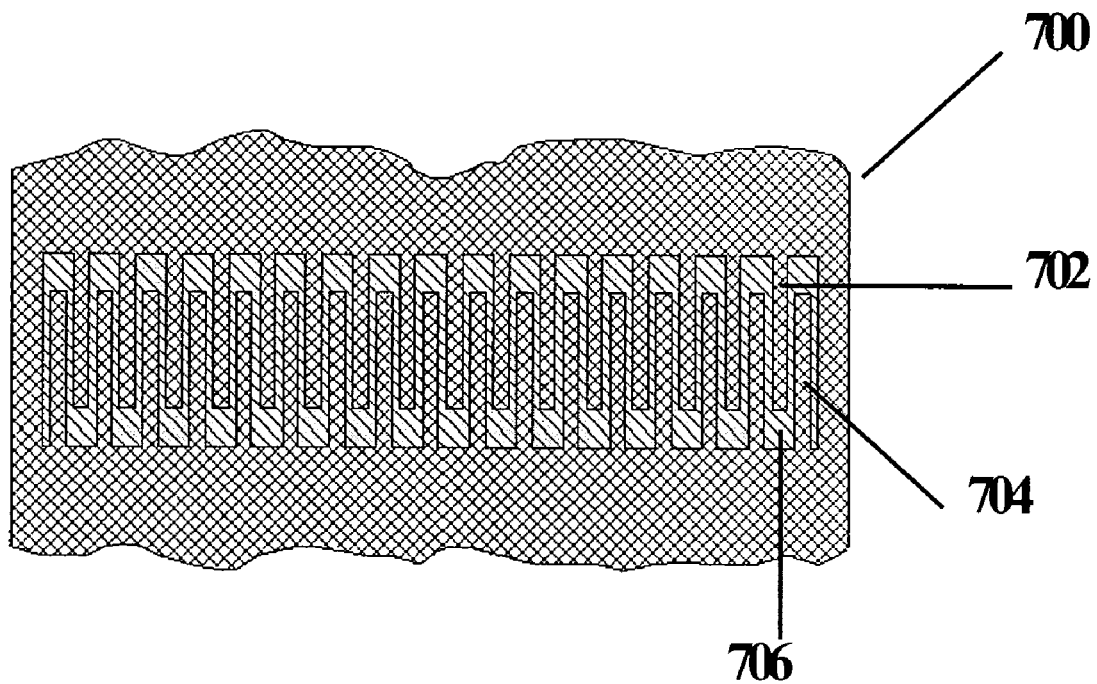

FIG. 7 shows a schematic diagram of the top view of yet another embodiment of a sensor of the invention comprising a MEMS device 700. The MEMS device forms the capacitive element of an L-R-C network (not shown). Two sets of immovable, interdigitated capacitive elements, 702 and 704, are formed within the MEMS device 700. The active material 706 (e.g., hydrogel) is disposed between the two sets of capacitive elements. This active material is chosen so that it responds to a measurand by a change in permittivity and, consequently, changes the capacitance of the device. Although swelling may also occur, this does not directly affect the capacitance.

Figure 8:
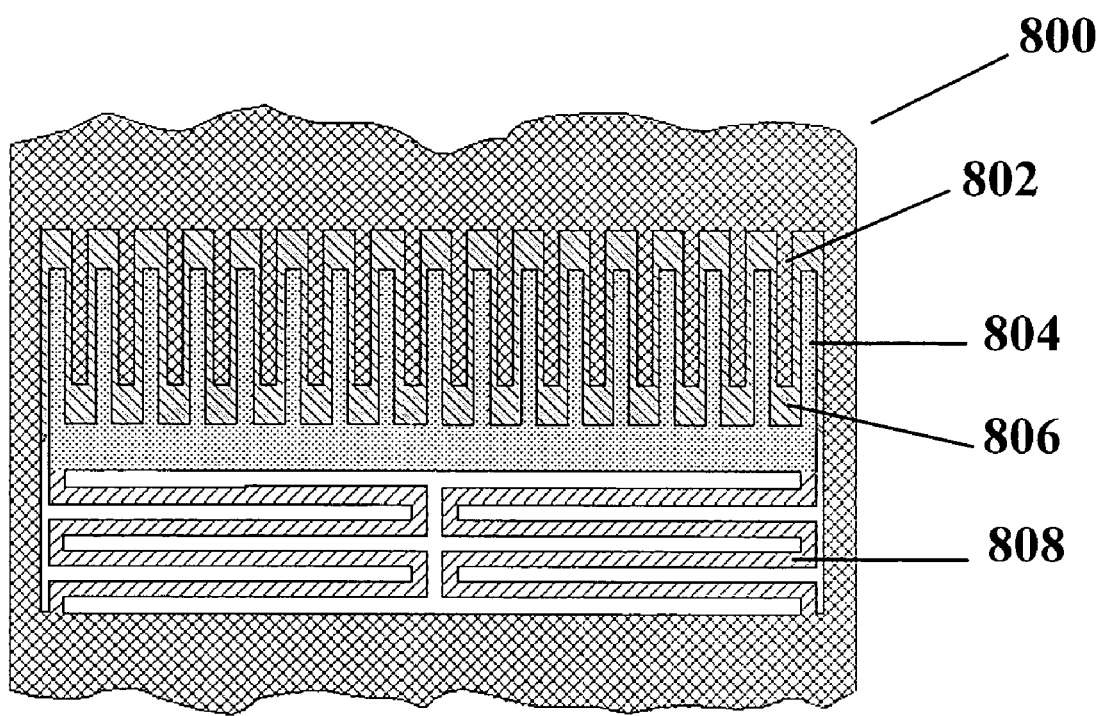

FIG. 8 shows a schematic diagram of the top view of a further embodiment of a sensor of the invention comprising a MEMS device 800. The MEMS device forms the capacitive element of an L-R-C network (not shown). Two sets of interdigitated capacitive elements, 802 and 804, are formed within the MEMS device 800 with the first of these, 802, fixed within the device and the second, 804, movably mounted on spring elements 808. The active material 806 (e.g., hydrogel) is disposed between the two sets of capacitive elements 802 and 804. This active material is chosen so that it responds to a measurand by swelling and by a change in its permittivity. Swelling is liable to be restricted by shear forces acting within the active material, between the interdigitated elements, however, some displacement of movable capacitive element 804 will occur. This movement can change the capacitance of the device in the same sense as the change that arises from the change in permittivity, thereby increasing the sensitivity of the MEMS capacitor 800.

5. DETAILED DESCRIPTION OF THE INVENTION

The present invention provides a low-cost, efficient, long-lived sensor for monitoring concrete that is powered and interrogated using radio frequency (RF) energy from a distance (e.g., a distance of over one meter) and that returns a unique identification ("ID") number so that data can be correlated with sensor location.

The invention provides a sensor for monitoring an environmental parameter in concrete comprising:
 (a) an enclosure for embedding in concrete;
 (b) a detecting means connected to the enclosure for detecting at least one environmental parameter in concrete, the detecting means comprising at least one capacitive element for measuring capacitive change;
 (c) an active material connected to the enclosure,
  (i) the active material being liable to respond to the environmental parameter, and
  (ii) the active material being operably connected to the capacitive element;
 (d) a RFID chip mounted within the enclosure, the RFID chip being operably connected to the detecting means; and
 (e) an antenna operably connected to the RFID chip,
  (i) the antenna being operably connected to the detecting means, and
  (ii) the antenna being part of an L-R-C circuit whose resonance frequency shifts within an assigned frequency band.

In another embodiment, the sensor further comprises a transceiver electromagnetically coupled with the antenna.

In another embodiment, the sensor further comprises an information processor in communication with the transceiver, the information processor being adapted to identify the environmental parameter from data generated by the transceiver. In another embodiment, the environmental parameter is identified by measuring a shift in frequency of complex impedance (Z) within the assigned frequency band.

In certain embodiments, the transceiver is operably connected (e.g., by a wired or wireless connection) to a means for measuring the change in resonance frequency (i.e., frequency shift) of the sensor's L-R-C circuit (where L is the antenna's inductance, R is resistance and C is capacitance).

In certain embodiments, the invention provides a passive sensor (i.e., a sensor that requires no external wiring or battery to provide power) that is embedded within concrete and that measures moisture content, temperature, pH and/or ion concentration (e.g., chloride, sodium or potassium) ions. In one embodiment, the passive sensor provides information starting with the initial quality control period of freshly mixed or freshly poured concrete. In another embodiment, it provides information throughout the period of useful service life of the concrete or throughout the period of deterioration and repair. In another embodiment, data obtained from the sensor of the invention may be used to prolong the service life of the concrete, lower infrastructure costs and promote development of more effective plans for remediation.

According to the invention, an environmental parameter in the concrete, for example, moisture content, temperature, pH or ion concentration (e.g., chloride, sodium or potassium ion), will produce a response in the active material. The active material is operably connected to the detecting means for capacitive change, and a response in the active material thereby produces a change in the capacitive element of the detecting means. The change in the capacitive element shifts the resonance frequency of the L-R-C network within an assigned frequency band of the antenna that is operably connected to the RFID chip. As disclosed hereinbelow, a diode in the antenna circuit may be used, in certain embodiments, to generate even harmonics so that the re-radiated signal can be separated from the input by a transceiver electromagnetically coupled with the antenna.

In certain embodiments, the transceiver is operably connected (e.g., by a wired or wireless connection) to a means for measuring the complex impedance (Z) within the assigned frequency band.

An information processor is in communication with the transceiver, and is adapted to identify the environmental parameter from data generated by the transceiver. In one embodiment, the environmental parameter is identified by measuring a shift in frequency of complex impedance (Z) within the assigned frequency band.

The invention also provides a MEMS-based capacitor that responds to an environmental parameter in concrete.

The invention also provides a method for applying an active material within a MEMS device comprising pouring at least one precursor material of the active material into an opening of the MEMS device. In one embodiment, the precursor material is a precursor for a hydrogel.

For clarity of disclosure, and not by way of limitation, the detailed description of the invention is divided into the subsections set forth below.

5.1 Enclosure for Embedding in Concrete

The lifetime of the sensor of the invention is indefinite, since, in certain embodiments, it is passive and no battery is required. The sensor of the invention comprises an enclosure for embedding in concrete, which protects the sensor from long-term exposure to the environment. Any material known in the art compatible with concrete may be used to construct the enclosure. e.g., concrete, ceramic materials, plastic, quartz, glass. In one embodiment of the invention, a planar, organic substrate is used.

In one embodiment, the enclosed sensor is embedded in the concrete aggregate. In another embodiment, the enclosed sensor is attached to a reinforcing element of the concrete, e.g., rebar.

In one embodiment, the enclosure is impermeable. In a specific embodiment, the impermeable enclosure encloses a temperature sensor.

In another embodiment, at least a portion of the enclosure is permeable (e.g., is perforated or microporous, or contains holes or openings) and permits ion migration or ingress of moisture.

In one embodiment, the enclosure is rigid. In another embodiment, the enclosure is flexible.

Given the moist, ionic environment in which the sensor of the invention must operate over a period of many years, in one embodiment, a ceramic enclosure is used. Ceramic enclosures can be hermetically sealed using glass or metal, using methods known in the art, so that the RFID chip, diode and wiring can be completely protected from moisture that might otherwise result in delaminations.

In one embodiment, the sensor is encapsulated within a hermetic package, e.g., a ceramic package. In such an embodiment, the antenna is small enough to be contained within the hermetic package. In another embodiment, the antenna is larger and is not contained within the hermetic package.

In embodiments of the invention in which a MEMS device is used (see Section 5.2), the MEMS device can be located, for example, within a cavity on or in the ceramic enclosure.

Since ceramics can never be completely densified, the resulting porosity may be used to facilitate bonding to cement. Alumina ceramics have a coefficient of thermal expansion (CTE) of about 6.5 ppm/° C., which is similar to that of limestone and some other aggregates, and may be used, in certain embodiments, to form enclosures for the sensor of the invention.

In another embodiment, at least a portion of the enclosure is silicone. In a specific embodiment, silicone encapsulation, a technique commonly known in the art, is used to provide short-term protection of the sensor, e.g., for use in testing prototypes of the sensor.

5.2 Detecting Means for Detecting Environmental Parameters in Concrete

In one embodiment, the sensor of the invention comprises a detecting means connected to (e.g., mounted within or mounted on the surface of) the enclosure for detecting at least one environmental parameter in concrete, the detecting means comprising at least one capacitive element for measuring capacitive change.

Environmental parameters in concrete include, but are not limited to moisture content, temperature, pH and concentration of ions (e.g., chloride, sodium or potassium ions).

In certain embodiments, the detecting means comprises a capacitor. The capacitor can be, e.g., an interdigitated capacitor or a parallel plate capacitor. In a specific embodiment, the capacitor is a perforated parallel plate detector.

In one embodiment, the capacitive change is effected by movement within the capacitive element (e.g., one side or plate of the capacitor moves). In another embodiment, the capacitive change is effected by change in permittivity of an active material (see Section 5.3). In yet another embodiment, both movement and a change in permittivity occur.

In a specific embodiment, the capacitor is a MEMS device. MEMS devices are well known in the art, e.g., a semiconductor device with mechanical features on the micrometer scale. In one embodiment, the sensor comprises a MEMS-based capacitor that responds to an environmental parameter in concrete.

The sensor of the invention also comprises an active material connected to (e.g., mounted within or mounted on the surface of) the enclosure (see Section 5.3). The active material is liable to respond to the environmental parameter and is operably connected to the capacitive element.

In one embodiment, when the active material responds to an environmental parameter in concrete, it produces a capacitive change in the capacitive element (e.g., capacitor or MEMS device).

In a specific embodiment, the active material is a hydrogel and the hydrogel is embedded in the MEMS device (see Section 5.3).

In another specific embodiment, the sensor comprises a MEMS cantilever resonator with a hydrogel coating. The MEMS cantilever resonator can be used, in certain embodiments, as an electro-mechanical device driven by an RF signal within an assigned frequency band.

In another embodiment, the active material is surrounded by a permeable layer capable of allowing moisture or ions to permeate into the active material. Such permeable layers are well known in the art and include, but are not limited to, polyimide, GORE-TEX®, porous ceramic and concrete.

Long-term exposure to the environment within concrete can cause severe corrosion of circuitry as the pH decreases. To overcome this problem, in certain embodiments the circuitry and connections to the MEMS device can simply be isolated from the environment, provided that the measurands can permeate into the active material. Alternatively, various platings well known in the art, including but not limited to nickel, chromium, gold and palladium, may be applied to the circuitry and antenna. This is especially important if the circuit carrier can absorb moisture (e.g., a polyimide circuit carrier).

5.3 Materials for Capacitive Measurements

The sensor of the invention comprises an active material connected to (e.g., mounted within or mounted on the surface of) the enclosure, (i) the active material being liable to respond to the environmental parameter, and (ii) the active material being operably connected to (e.g., in physical contact with, surrounding, or coating) the capacitive element.

In one embodiment, the active material is in physical contact with a capacitive element that is movable. In another embodiment, the active material is in physical contact with a capacitive element that is fixed, and the active material changes permittivity in response to an environmental parameter. In another embodiment, the active material is not in physical contact with a capacitor but is movably connected with the capacitor via a movable member, such as a spring or a movable plate.

In certain embodiments, the active material is enclosed or surrounded by a permeable barrier, e.g., a permeable layer. In one embodiment, the active material is partially enclosed by the permeable barrier. In another embodiment, the active material is completely enclosed by the permeable barrier.

In one embodiment, the active material is a dielectric material. Dielectric materials can be used for capacitive temperature, moisture content, pH and chloride (or sodium or potassium) ion measurements and are well known in the art (see, e.g., Ong, Zeng and Grimes, "A Wireless, Passive Carbon Nanotube-based Gas Sensor", IEEE Sensors Journal, 2, 2, (2002) 882-88; Ong, Grimes, Robbins and Singh, "Design and application of a wireless, passive, resonant-circuit environmental monitoring sensor," Sensors and Actuators A, 93 (2001) 33-43).

Dielectric materials that respond in a predictable, stable way to changes in moisture content, temperature, pH or ion (e.g., chloride, sodium or potassium) concentration over a long period may be identified according to methods well known in the art. In a specific embodiment, polyimide, which responds to moisture, is used as the active material.

Dielectric materials that respond to pH are well known in the art and include, but are not limited to: PMMA, poly(2-hydroxyethyl methacrylate (HEMA)) and hydrogels such as copolymerized N-isopropyl acrylamide (NIPAAm) and acrylic acid (AAc). In one embodiment, acrylic acid (AAc), which is sensitive over the range of 2-12, is used.

Other hydrogels commonly known in the art and suitable for use in the sensor of the invention include, but are not limited to poly(2-hydroxypropyl methacrylate) and poly(allylamine hydrochloride).

Polyampholytic hydrogels and bilayer lipid membranes are well known in the art (English, Mafé, Manzanares, Yu, Grosberg and Tanaka, Equilibrium Swelling Properties of Polyampholytic Hydrogels, J. Chem. Phys., 104, 21 (1996) 8713-8720; Tien, Barish, Gu and Ottova, Supported Bilayer Lipid Membranes as Ion and Molecular Probes, Analytical Sciences 14, (1998) 3-18). Such hydrogels or bilayer lipid membranes may also be used, in certain embodiments, as active materials to detect changes in environmental parameters such as ion concentration.

In certain embodiments, bacterial growth or contamination is prevented from occurring in the active material by using anti-bacterial methods well known in the art, e.g., adding an anti-bacterial agent to the active material before (or after) it is introduced into the sensor.

In certain embodiments, a dielectric material for use in the sensor of the invention is coated onto the capacitive element (e.g. an interdigitated or parallel plate capacitor, a MEMS device) using standard techniques practiced in the electronics industry. For example, wet coating and blade leveling can be used to prepare thick dielectric layers. Processes well known in the art, e.g., spin-coating, can be used to produce uniform, thin layers for testing.

Precursors of the active material can be mixed in situ to fill spaces within, or in contact with, the capacitive element (e.g., a MEMS device). In one embodiment, the invention provides a method for applying an active material within a MEMS device comprising pouring at least one precursor material of the active material into an opening of the MEMS device. In another embodiment, the precursor material is a precursor for a hydrogel. Such precursor materials are commonly known in the art.

In testing a dielectric material for potential use with a capacitive element, layer thickness can be varied in order to study the sensitivity and response time of each dielectric to the measurands. A full-factorial experiment can be carried out for the four measurands-moisture content, temperature, pH and chloride (or sodium or potassium) ion concentration-according to methods well known in the art.

Furthermore, in testing a dielectric material for potential use with a capacitive element, moisture content can be varied from 1 to 100% R.H.; temperature can be varied from −30° C. to 70° C.; pH range can be varied from 6 to 13 and chloride concentration can be varied from 0.2 to 4 mg/cm$^3$ (corresponding roughly to industry limits of 0.06% to 1% Cl— by weight). In one embodiment, the capacitive element has a capacitance of about 20 pf for a typical LC at 13.5 MHz.

In testing a dielectric material for potential use with a capacitive element, capacitance tests can be undertaken in a controlled environment. Initial temperature and moisture tests may be made, for example, in a controlled environment, such as a temperature and humidity ("T & H") chamber, according to methods well known in the art.

Additional tests can be performed within a dielectric material so that moisture content, pH and ion concentration (e.g., chloride, sodium or potassium ion concentration) can be easily varied. Capacitance can be measured according to standard methods, e.g., using a digital capacitance tester with a range of, e.g., 2 pF to 200 nF and a resolution of e.g., 0.001 pF to 0.1 nF. Capacitance changes can be correlated to measurements made using standard techniques.

A hygrometer can be used to measure moisture content using standard techniques. A solid-state FET tester can be used, using standard techniques, to measure pH, while Cl(—) concentration can be measured, using standard techniques, e.g., the chloride ion selective electrode method.

5.4 RFID Devices

The invention provides a sensor that comprises a RFID chip mounted within the enclosure, the RFID chip being operably connected to the detecting means. The RFID chip may be connected to the detecting means by any art-known method, e.g., wired to, or connected by a wireless method to, the detecting means.

RFID systems are wireless systems that permit non-contact reading and that are commonly known in the art. An RFID system comprises an RFID chip, an antenna that is part of an L-R-C network and a transceiver. Amplitude modulation of a RF signal by the RFID system is used to provide identification of the concrete sensor of the invention.

In one embodiment, the RFID chip uses only basic modulation circuitry, a rectification bridge and non-volatile memory. Such RFID chips are well-known in the art.

Standard, commercially available RFID chips are designed to modulate a source signal continuously. In certain embodiments, the sensor comprises a standard RFID chip (e.g., available from Alien Technology, Morgan Hill, Calif.; Microchip Technology Inc., Chandler, Ariz.; Graphic Solutions Inc., Burr Ridge, Ill.; or Poynting Innovations (Pty) Ltd, Wendywood, South Africa). Accurate determination of the shift in resonance frequency in such standard chips is simplified, since sidebands or harmonics are well outside the band and are generally reduced.

In one embodiment, the sensor comprises an RFID chip that is modified, according to methods well known in the art, so that it provides single-shot data modulation. In another embodiment, the sensor comprises an RFID chip that is custom-programmable In one embodiment, the sensor comprises an RFID system with one-way communication between the RFID transponder (e.g., the RFID chip and antenna) and a transceiver. In one aspect of this embodiment, a dipole antenna or a coil antenna (depending on the operating frequency) is operably connected to, and powers, the RFID chip when current is induced in the antenna by an RF signal from the transceiver's antenna.

In another embodiment, the sensor of the invention operates within RF bands designated by a national authority as RFID operating bands. For example, in the United States, designated RFID operating bands of 125 KHz, 27.125 MHz, 13.56 MHz or 2.45 GHz, may be used for powering and/or interrogating the RFID chip.

In another embodiment, one or more sensors of the invention are located within the concrete. To prevent the multiple sensors from interacting with one another and garbling the data, an anti-collision scheme may be used. Such anti-collision schemes are well known in the art, such as time-based anti-collision schemes using, e.g., a programmable, sleep-mode duration RFID chip (e.g., MCRF 355/360 RFID microchip from Microchip Technology Inc., Chandler Ariz., see Microchip Technology Inc.'s Technical Bulletin DS21287F for discussion of anti-collision scheme).

In another embodiment, the RFID system comprises a diode. A diode within a resonant circuit produces even harmonics owing to its nonlinear response. This has been exploited in some RFID systems in which RF excitation at 2.45 GHz is re-radiated and detected at 4.9 GHz (Pohl and Reindl, New Passive Sensors, Proceedings of the IMTC, Venice, Italy (1999) 1251-1255). A diode in the antenna circuit of the RFID system may be used to generate harmonics so that the re-radiated signal can be separated from the input. For example, a diode in the antenna circuit may be used so that RF excitation at 13.56 MHz is re-radiated at 27.125 MHz.

Figure 1:
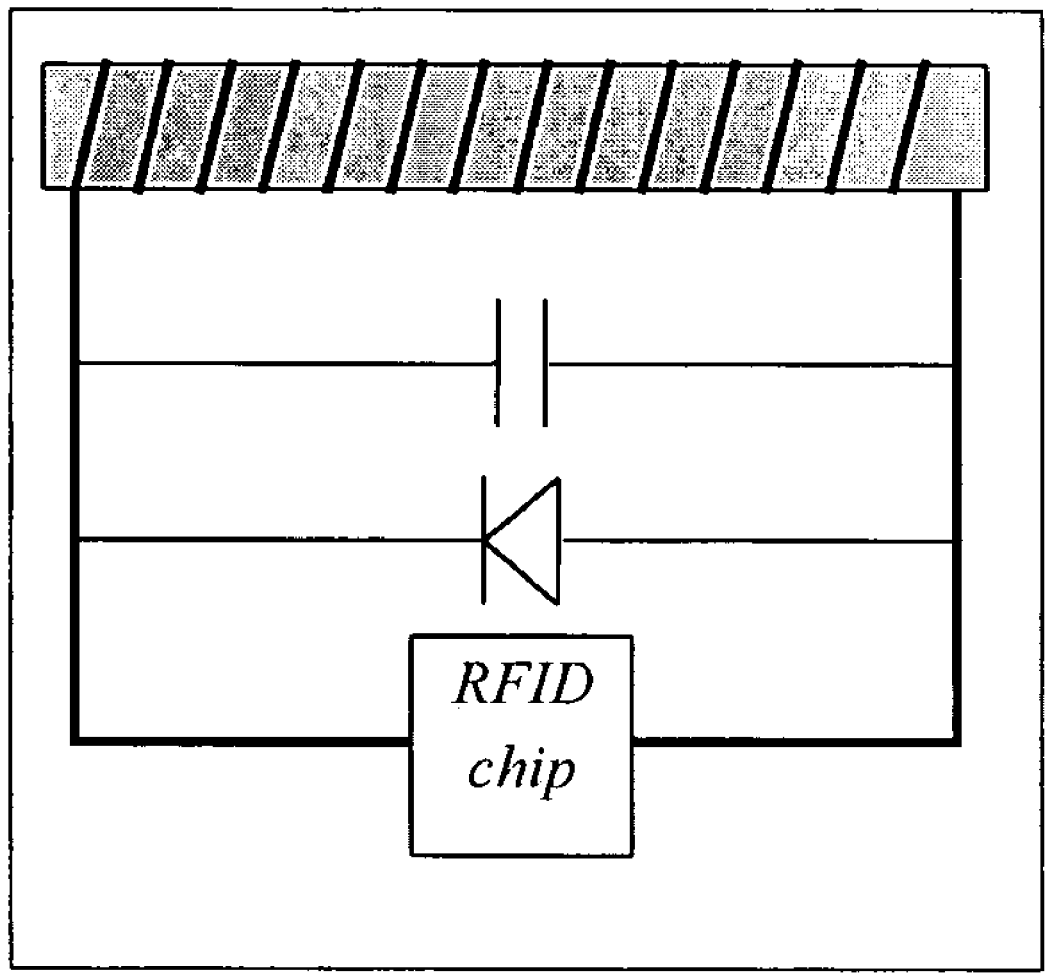

FIG. 1 shows a schematic diagram of an embodiment of the sensor of the invention. In this embodiment, the sensor comprises a RFID chip, a ferrite core antenna, a capacitive element and a diode. The diode produces even harmonics of the excitation frequency.

In one embodiment, the shift in resonance frequency is a shift in frequency of the re-radiated second harmonic produced by the RFID chip. In a specific embodiment, the RFID operating bands used are 13.56 MHz for power and interrogation and 27.125 MHz for the re-radiated signal.

According to the present invention, the RFID chip is operably linked with a detecting means that modifies the complex impedance (Z) of the resonant antenna circuit, to indicate an environmental parameter such as moisture content, temperature, pH or ion (e.g., chloride, sodium or potassium) concentration. It is well known in the art that capacitors can be used to modify the frequency of a re-radiated RF signal. The MEMS capacitors described hereinabove in Section 5.2 modify the Z in this manner.

In another embodiment, modulation of the re-radiated signal carries the sensor's identification signal (e.g., an identification number) for a limited duration of (e.g., once). In another embodiment, modulation of the re-radiated signal carries the device ID for as long as the device receives power.

In one embodiment, the invention provides a sensor that is powered and interrogated by a transceiver using RF energy from a distance, e.g., a distance of 0.1-1 meter, 1-5 meters, 5-10 meters, or greater than 10 meters. For example, at 125 KHz, the range is 0.1-0.25 meter; at 13.5 MHz, the range is 0.25-0.5 meter; at 915 MHz, the range is 0.5-1 meter; and at 2.4 GHz, the range is 1-2 meters.

5.4.1 Capacitance Measurement Using RFID Frequency Shift

An RFID chip is a powerless device that can transmit data that has been preprogrammed into its memory. The method used to extract data from such a device requires two steps. The first step is to power the device with an RF frequency. This is fairly simple to do. A high-Q, LC circuit comprising an inductor (L, the antenna), and a capacitor (C) are arranged nearby, and connected to, the RFID chip. Then another (reader) antenna is brought near to the RFID assembly. The magnetic field is picked up by the RFID antenna, a voltage is induced in its antenna and rectified inside the RFID chip, thereby powering the RFID device. Read distance is frequency dependent and proportional to the diameter of the reader antenna by $1/\sqrt{2}$. The reader antenna can be thought of as the primary coil of a transformer whereas the RFID antenna is the secondary and the air between them is the coupling medium.

The second step in RFID communication occurs with the actual data transmission after the device has achieved sufficient power. The typical data detection method is to detect the back scatter modulation from the RFID chip. Back scatter modulation is achieved by repeatedly shunting the antenna coil at the RFID device. Since the reader antenna coil and the RFID antenna coil, essentially form the primary and secondary windings of a transformer, a momentary shunt at the secondary causes a voltage drop at the primary which is detected by the reader. The signal is typically very small, perhaps 100 mV on a 100 volt signal.

It is possible to shift the LC center frequency by adding or subtracting capacitance from the high Q circuit. The change in capacitance can come, in certain embodiments, from a MEMS device whose capacitance changes with a desired measurand. This can be accomplished by using the MEMS device as part of the LC circuit. In calibration, the capacitance change per unit of measure will be established. The task then becomes one of measuring the additional capacitance using center frequency shift.

Shifting the resonance frequency reduces the power that can be transmitted to the RFID chip. A method for detecting the new resonance frequency is to sweep a fixed range of excitation frequencies looking for the best response from the RFID device. Since the RFID signal is detected by measuring a change in the voltage at the reader, the best frequency will be indicated by the maximum voltage change at the reader. The reader signal can be visualized as Amplitude Modulated by the RFID device and the signal envelope is the demodulated signal. The frequency with the minimum envelope is the new resonance frequency.

A means commonly known in the art to realize this type of detection is to build a reader with the ability to sweep a fixed frequency range. This may be done by methods commonly known in the art, such as using a voltage controlled oscillator (VCO) driven by a step, sawtooth, or ramp signal. A new output frequency would correspond to each new input voltage.

The rate of change of the frequency should be very low, so that several hundreds of cycles of each new frequency are fed to the RFID device. This is required because the RFID device needs these cycles to charge its internal circuitry and execute initialization before sending its data back. With each new frequency, the change in the primary voltage will be measured.

The process will be stopped once a maximum amount of voltage drop at the reader has been found at a particular frequency. Then the new center frequency can be measured or the voltage at the input to the VCO can be used to indicate the new center frequency. Once this center frequency is found, it must be subtracted from the original center frequency to determine the difference from which the change in capacitance can be calculated. The change in capacitance then yields the change in the unit of measure.

A nonlinear change in capacitance can be accommodated with a look-up-table (LUT) generated from calibration data, a common art-known method.

The above circuit may be realized without a controller by the proper connection of a ramp generator, VCO, peak detector, antenna circuit, and output display. However, in certain embodiments, the addition of a microcontroller will allow the ability to fine-tune the center frequency detection and repeatedly verify that this is the correct frequency. In certain embodiments, the LUT may be stored on the microcontroller and corrected readings given via analog or digital outputs.

Figure 2:
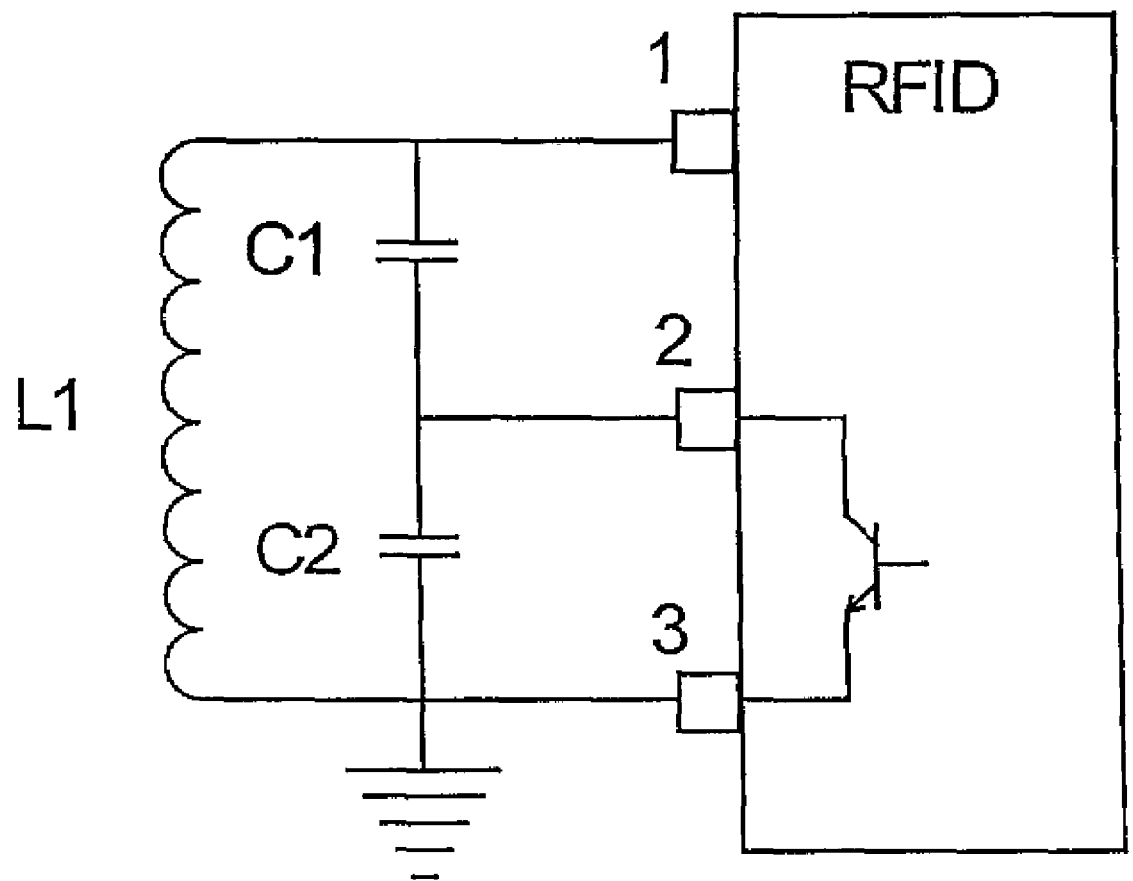

FIG. 2 shows an RFID antenna-capacitor circuit for use in one embodiment of the sensor of the invention. L1 is the sensor antenna coil, C1 is a fixed capacitor, C2 is the variable capacitance formed by the sensor, which is the variable capacitor sensitive to the environment. C2 is switched out of the resonant circuit by the RFID chip using the internal transistor as it transmits its data. This action causes the resonance of the LC circuit formed by the antenna and capacitors to change, the change from resonance to non-resonance is detected at the reader as a voltage drop in the source antenna. However, it is the shift of the primary resonant frequency that allows the measurement a change in capacitance at C2. That is, the difference between the theoretical center frequency with C2 at some nominal value and the frequency at which the actual resonant frequency is found. This difference is used to infer a difference in capacitance at C2 and therefore a proportional difference in the environment. See Section 5.4.1 for details.

5.5 Design of Antenna and Transceiver

The sensor of the invention comprises an antenna operably connected to (e.g., wired to) the RFID chip. According to the invention, the antenna is operably connected (e.g., wired to) to the detecting means, and the antenna is tuned to an assigned frequency band and is part of an L-R-C circuit whose resonance frequency shifts within the assigned frequency band. A change in resonance frequency is characterized by a change in the amplitude of the source signal at the original resonance frequency.

As disclosed above, national authorities assign frequency bands to be used with RFID chips. For example, in the United States, RFID devices are generally designed to operate within the assigned frequency bands of 125 KHz, 3.56 MHz, 27.125 MHz or 2.45 GHz. In one embodiment, the invention provides a sensor wherein the assigned frequency band is 13.56 MHz and the re-radiated signal is within a frequency band 27.125 MHz.

According to the invention, an antenna is used to detect an RF signal emitted from an RFID system in one or more concrete sensors of the invention. A number of designs for antennas are known in the art and may be evaluated for use in the present invention with respect to their sensitivity, range, directionality and robustness, according to methods well known in the art. Antennas may be designed, according to principles well known in the art, to maximize the range and sensitivity of the RFID system.

Antennas suitable for use according to the invention include, but are not limited to, loop antennas, coil antennas and dipole antennas. In one embodiment, the antenna is mounted within the enclosure. In other embodiments, the antenna is mounted on the outside of the enclosure or is located external to the enclosure. In another embodiment, the antenna is wrapped around the enclosure.

In one embodiment, the source supply and receiving antennas are two separate devices. Such two-antenna monitoring approaches are commonly known in the art (see, e.g., Ong, Grimes, Robbins and Singh, "Design and application of a wireless, passive, resonant-circuit environmental monitoring sensor," Sensors and Actuators A, 93 (2001) 33-430).

Coil antennas may be used if the operating frequency of the concrete sensor is not in the GHz range. If the operating frequency is in the GHz range, a simple wire may be used as an antenna.

Dipole antennas are highly directional. In embodiments in which a dipole antenna is employed, any method known in the art may be used to align the dipole antenna. In one embodiment, a sensor of the invention comprising a dipole antenna is mounted in a specific orientation on rebar, thereby aligning the dipole antenna in the specific orientation.

In one embodiment, a loop antenna is used. Loop antennas generate a magnetic flux that may be expressed using the Biot-Savart equation as shown in the upper portion of FIG. 3, where A is the antenna surface area, $\mu_o$ is the magnetic field constant, $I_R$ and $r_R$ are the current and radius of the reader's antenna and x is the distance at which the flux is measured.

In certain embodiments, the flux can be significantly increased by using a ferromagnetic core.

In the lower portion of FIG. 3, the term $\mu_R$ represents the permeability of the core material. For either antenna design depicted (loop antenna (top half of diagram) or ferrite-core antenna), the magnetic flux increases with current, number and diameter of turns, and decreases with distance from the antenna, while the voltage induced in the reader's coil is proportional to the rate of change in flux, $v = N \cdot d\Phi/dt$.

This coupling between the two antennas can be expressed by the impedance equation, $$Z = Z_R + \frac{\omega^2 M^2}{Z_T},$$

where w is the circular frequency, M the mutual inductivity and $Z_T$ the impedance of the transponder. The impedance of the reader can be measured without the presence of the transponder and removed from the equation during tests.

Figure 4:
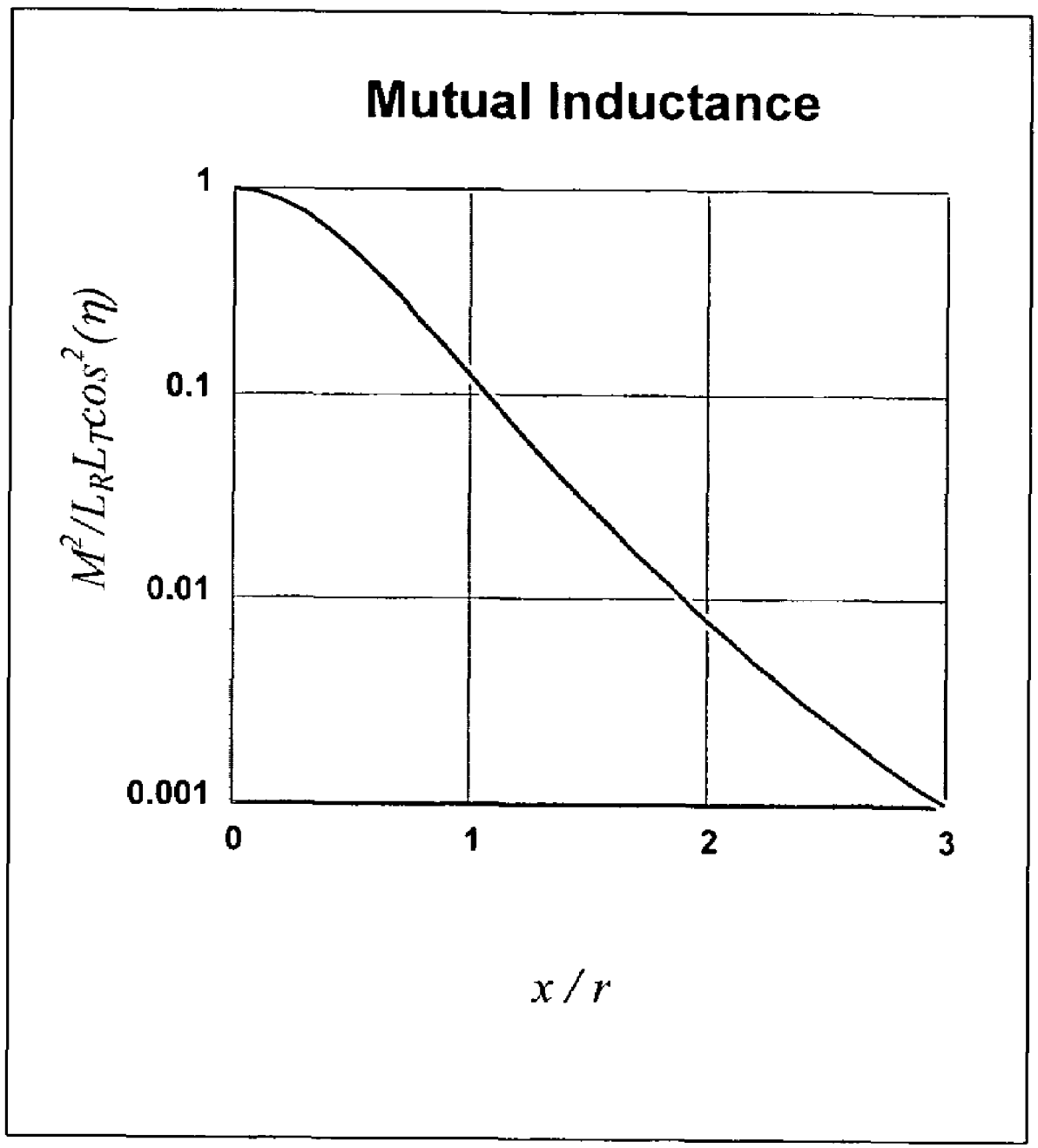
FIG. 4 is a diagram showing that the impedance of two coupled coils is a function of the mutual inductance, M, which falls rapidly as the distance x between the coils becomes larger than the coil diameters, r. See Section 5.5 for details.

From basic transformer theory, the mutual inductivity M is expressed by $$M^2 = L_R L_T \cos(\theta) \left[ \frac{r_R r_T}{(r_R^2 + x^2)} \right]^3$$

where L is an inductance, r is the radius of one of the loop antennas and x and θ are the distance and angle between them. Subscripts R and T indicate reader and transponder respectively. This function is strongly dependent on the ratio of antenna diameters to distance between them. If the two antennas have identical diameters, the function $M^2$ varies as shown in FIG. 4.

Using an RLC model of the transponder antenna, the impedance measured at the reader can be written as $$Z - Z_R = \frac{\omega^2 M^2 R}{(R - \omega^2 RLC)^2 + \omega^2 L^2} + j \frac{\omega^2 M^2 [\omega RC(R - \omega^2 RLC) - \omega L]}{(R - \omega^2 RLC)^2 + \omega^2 L^2}.$$

The real part of the impedance reaches a peak when its derivative is zero $\omega_r = \sqrt{1/LC}$ while the imaginary part crosses zero at $\omega_i = \sqrt{(1/LC)-(1/RC)^2}$. The values of L and C can be determined from the complex impedance as long as $M^2$ does not become too small.

The antenna preferably has a rigid support, so that it is not damaged during concrete pouring. Such supports are well known in the art, and include, but are not limited to, a ceramic-coated ferrite core (which would significantly increase the operating range but be much more directional) and a non-magnetic material.

The sensor of the invention comprises a transceiver electromagnetically coupled with the antenna. A number of designs for transceivers are known in the art and may be evaluated for use in the present invention with respect to their sensitivity, range, directionality and robustness, according to methods well known in the art.

In certain embodiments, the transceiver is operably connected (e.g., by a wired or wireless connection) to a means for measuring a frequency shift within the assigned frequency band. In one embodiment, the transceiver is operably connected (e.g., by a wired or wireless connection) to a means for measuring the complex impedance (Z) within the assigned frequency band. Means for measuring complex impedance (Z) are commonly known in the art, e.g., an 4395A Impedance Analyzer from Agilent Technologies (Palo. Alto, Calif.).

In one embodiment, the means for measuring a frequency shift within the assigned frequency band detects a change in the complex impedance (Z) of the transceiver. In another embodiment, it detects a re-radiated signal at a harmonic frequency.

In one embodiment, the transceiver transmits over a range of frequencies centered on 13.56 MHz and the sensor's antenna is designed to have the highest possible Q-factor. The design of components with high Q's are well known in the art.

In another aspect of this embodiment, an antenna tuned to 27.125 MHz has a lower Q, in order to efficiently detect the second-harmonic signal as its frequency is shifted by the sensor.

In another embodiment, the sensor comprises a diode within a resonant circuit that produces harmonics owing to its nonlinear response. In certain aspects of this embodiment, the RF excitation is 13.56 MHz and the re-radiated emission is detected at 27.125 MHz.] RF excitation and reradiation is well known in the art (see, e.g., Pohl and Reindl, "New Passive Sensors", Proceedings of the IMTC, Venice, Italy (1999) 1251-1255).

Since many active materials respond simultaneously to two or more measurands, both capacitors shown in FIG. 2 may be MEMS devices using different active materials. By determining two capacitances, the two measurands can be separated.

5.6 Data Collection

In certain embodiments, the sensor of the invention comprises an information processor (e.g., a personal computer or a hand-held personal digital assistant (PDA)) in communication (i.e., connected by any art-known wired or wireless connection) with the transceiver. The information processor may be adapted to identify the environmental parameter from data generated by the transceiver, using any art-known information processing methods, e.g., an information processing program, conventional computer programming methods, etc. In one embodiment, the environmental parameter is identified by measuring a shift in complex impedance (Z) of the transceiver within the assigned frequency band.

The invention provides a sensor that returns a unique identification number so that the data collected can be correlated with the sensor's location. In a specific embodiment, data is read by frequency analysis of one or more RLC antennas in the device, whose resonance frequencies is altered by a change or response in the active material (see Section 5.4.1).

5.7 Characterization and Testing of the Concrete Sensor

Characterization and testing of the sensor of the invention can be carried out according to methods well known in the art. For example, a sensor's performance can be evaluated over a range of the applications shown in Table 1. To test the sensor's performance in evaluating raw materials, the sensor can be used, e.g., to estimate temperature, moisture content, and chloride content of aggregates, pH of mix water, and to collect temperature-time and pH-time data for cement after the addition of water. Comparisons can be made to current methods known in the art for monitoring concrete (e.g., thermometry, electronic pH meters, chloride content test ASTM C114). In certain instances, a brief field evaluation can be conducted after testing, according to methods well known in the art.

Fresh concrete determination can include, for example, a temperature-time determination (for maturity method calculations), and a moisture content determination to determine the water content of the fresh concrete. Control batches can be cast in the laboratory according to methods well known in the art.

A sensor of the invention that responds to chloride ion concentration can be assessed, according to standard methods, to determine its ability to discern chloride content. For example, fresh concrete can be intentionally doped with various concentration of $CaCl_2$ (the most commonly used set-accelerating admixture).

Hardened concrete samples can be immersed in a moist, high chloride content environment to monitor temperature, moisture content, and chloride content over time. Similar specimens can be placed in a chamber with an elevated $CO_2$ partial pressure, to force carbonation and thus force a drop in pH. The response over time of a sensor of the invention to pH may be compared to the traditional method of using a phenolphthalein indicator on a freshly exposed concrete surface.

The following examples are offered by way of illustration and not by way of limitation.

6. EXAMPLES

FIG. 5 is a schematic diagram of the top view of an embodiment of a sensor of the invention comprising a MEMS device 500. The MEMS device forms the capacitive element of an L-R-C network (not shown). Two sets of interdigitated capacitive elements, 502 and 504, are formed within the MEMS device 500 with the first of these, 502, fixed within the device and the second, 504, movably mounted on spring elements 508. The active material 506 (e.g., hydrogel) is disposed within and between the spring elements 508. This active material is chosen so that it responds to a measurand by swelling. As swelling occurs, capacitive element 504 moves relative to the fixed capacitive element 502, thereby changing the capacitance of the device. An important feature of this embodiment is the degree to which the active material 506 is constrained. The ratio of the surface bounded by the body of the MEMS device 500, the spring elements 508 and the movable capacitive element 504 to the free surface above and below the active material 506 is extremely high. As a consequence, the force that can be exerted by the active material is extremely high.

FIG. 6 shows a schematic diagram of the top view of another embodiment of a sensor of the invention comprising a MEMS device 600. The MEMS device forms the capacitive element of an L-R-C network (not shown). Two sets of interdigitated capacitive elements, 602 and 604, are formed within the MEMS device 600 with the first of these, 602, fixed within the device and the second, 604, movably mounted on spring elements 608. The active material 606 (e.g., hydrogel) is disposed between the main body of the MEMS device 600 and the movable capacitive element 604. This active material is chosen so that it responds to a measurand by swelling. As swelling occurs, capacitive element 604 moves relative to the fixed capacitive element 602, thereby changing the capacitance of the device. An advantage of this embodiment is the ease with which the active material 606 can be deposited. There is, however, a reduction in the amount of force that can be applied to movable capacitive element 604, due to the reduction in the degree of constraint in material 606.

FIG. 7 shows a schematic diagram of the top view of yet another embodiment of a sensor of the invention comprising a MEMS device 700. The MEMS device forms the capacitive element of an L-R-C network (not shown). Two sets of immovable, interdigitated capacitive elements, 702 and 704, are formed within the MEMS device 700. The active material 706 (e.g., hydrogel) is disposed between the two sets of capacitive elements. This active material is chosen so that it responds to a measurand by a change in permittivity and, consequently, changes the capacitance of the device. Although swelling may also occur, this does not directly affect the capacitance.

FIG. 8 shows a schematic diagram of the top view of a further embodiment of a sensor of the invention comprising a MEMS device 800. The MEMS device forms the capacitive element of an L-R-C network (not shown). Two sets of interdigitated capacitive elements, 802 and 804, are formed within the MEMS device 800 with the first of these, 802, fixed within the device and the second, 804, movably mounted on spring elements 808. The active material 806 (e.g., hydrogel) is disposed between the two sets of capacitive elements 802 and 804. This active material is chosen so that it responds to a measurand by swelling and by a change in its permittivity. Swelling is liable to be restricted by shear forces acting within the active material, between the interdigitated elements, however, some displacement of movable capacitive element 804 will occur. This movement can change the capacitance of the device in the same sense as the change that arises from the change in permittivity, thereby increasing the sensitivity of the MEMS capacitor 800.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A sensor for monitoring an environmental parameter in concrete comprising:
    (a) an enclosure for embedding in concrete;
    (b) a detecting means connected to the enclosure for detecting at least one environmental parameter in concrete, the detecting means comprising at least one capacitive element for measuring capacitive change;
    (c) an active material connected to the enclosure,
        (i) the active material being liable to respond to the environmental parameter, and
        (ii) the active material being operably connected to the capacitive element;
    (d) a RFID chip mounted within the enclosure, the RFID chip being operably connected to the detecting means;
    (e) an antenna operably connected to the RFID chip,
        (i) the antenna being operably connected to the detecting means, and
        (ii) the antenna being part of an L-C circuit whose resonance frequency shifts within an assigned frequency band, and
    (f) a transceiver electromagnetically coupled with the antenna,
wherein the transceiver is operably connected to a means for measuring the change in resonance frequency of the sensor's L-C circuit.

2. The sensor of claim 1 wherein the shift in resonance frequency is a shift in frequency of a re-radiated signal.

3. The sensor of claim 1 wherein the capacitive change is effected by movement of the capacitive element.

4. The sensor of claim 1 wherein the capacitive change is effected by change in permittivity of the active material.

5. The sensor of claim 1 wherein the capacitive element comprises a parallel plate capacitor.

6. The sensor of claim 1 wherein the parallel plate capacitor is a perforated parallel plate capacitor.

7. The sensor of claim 1 wherein the capacitive element comprises an interdigitated capacitor.

8. The sensor of claim 1 wherein at least a portion of the enclosure is permeable.

9. The sensor of claim 1 wherein the environmental parameter is moisture content.

10. The sensor of claim 1 wherein the environmental parameter is temperature.

11. The sensor of claim 1 wherein the environmental parameter is pH.

12. The sensor of claim 1 wherein the active material is a dielectric material.

13. The sensor of claim 1 wherein the active material is a hydrogel.

14. The sensor of claim 1 wherein the assigned frequency band is 13.56 MHz and the re-radiated signal is within a frequency band 27.125 MHz.

15. The sensor of claim 1 further comprising:
(g) an information processor in communication with the transceiver, the information processor being adapted to identify the environmental parameter from data generated by the transceiver.

16. The sensor of claim 15 wherein the environmental parameter is identified by measuring a shift in frequency of complex impedance (Z) within the assigned frequency band.

17. The sensor of claim 1 wherein the environmental parameter is ion concentration.

18. The sensor of claim 17 wherein the ion is chloride.

19. The sensor of claim 17 wherein the ion is sodium.

20. The sensor of claim 17 wherein the ion is potassium.

* * * * *